United States Patent
Fricker et al.

(10) Patent No.: US 7,262,341 B1
(45) Date of Patent: Aug. 28, 2007

(54) HYBRID SEASHORE PASPALUM AVAILABLE FROM SEED CALLED 'SEA SPRAY'

(75) Inventors: Crystal Fricker, Canby, OR (US); Joseph K. Wipff, Canby, OR (US); Ronny R. Duncan, San Antonio, TX (US)

(73) Assignees: Pure Seed Testing, Inc., Canby, OR (US); University of Georgia Research Foundation, Inc., Athens, GA (US)

( * ) Notice: Subject to any disclaimer, the term of this patent is extended or adjusted under 35 U.S.C. 154(b) by 246 days.

(21) Appl. No.: 10/941,151

(22) Filed: Sep. 14, 2004

(51) Int. Cl.
*A01H 5/00* (2006.01)
*A01H 5/10* (2006.01)
*A01H 1/00* (2006.01)

(52) U.S. Cl. ...................................... 800/298; 800/260

(58) Field of Classification Search ................ 800/260, 800/298
See application file for complete search history.

(56) References Cited

U.S. PATENT DOCUMENTS

PP12,625 P2 * 5/2002 Duncan

OTHER PUBLICATIONS

Turf-Seed, Inc., Pure Seed Testing, Inc., *Field Day 22*, Jun. 17, 2004, Front cover and pp. 148-150.

* cited by examiner

*Primary Examiner*—David H. Kruse
*Assistant Examiner*—Keith O. Robinson
(74) *Attorney, Agent, or Firm*—Klarquist Sparkman, LLP

(57) ABSTRACT

A seashore paspalum (*Paspalum vaginatum* O. Swartz) cultivar that can be propagated from seed is disclosed. In one example, the cultivar is known as 'Sea Spray'. Also disclosed is seed used to produce the grass, and methods of using the grass plant. In some examples, this grass is suitable for use in turf where alternative water resources are used to care for the turf.

11 Claims, No Drawings

HYBRID SEASHORE PASPALUM AVAILABLE FROM SEED CALLED 'SEA SPRAY'

FIELD

This disclosure relates to a seashore paspalum (*Paspalum vaginatum* O. Swartz) that is available from seed. One particular example of this grass is known as 'Sea Spray'.

BACKGROUND

Seashore paspalum (*Paspalum vaginatum* O. Swartz) is a perennial, rhizomatous and stoloniferous grass that resembles bermudagrass (*Cynodon dactlyon* (L.) Person). The grass ranges from very coarse ornamental types, to coarse types resembling St. Augustine grass (*Stenotaphrum secundatum* (Walters) Kuntze), to intermediate types resembling common bermudagrass, to very fine types like hybrid Bermudagrass. Seashore paspalum grass takes on a chameleon-like nature as the mowing height is lowered, transforming from longer internodes and wider leaves during the grow-in phase to very short internodes and smaller, finer leaves when the mowing height reaches 3 mm (⅛ inch). Seashore paspalum has a darker green color than most bermudagrass when mowed at the same height as bermudagrass. The leaves have a heavy wax load on them that gives the appearance of a glistening, shiny green luster. The appearance resembles Kentucky bluegrass (*Poa pratensis* L.) and the grass has a similar pattern of mower striping. This is a warm-season grass that is native to tropical and sub-tropical regions worldwide. Seashore paspalum grows naturally in coastal environments, often found in brackish marsh water or in close proximity to ocean waters. It also grows in areas that receive extended periods of heavy rains and low light intensity.

Although seashore paspalum has been in existence for thousands of years, its use for landscapes, athletic fields, and golf courses has occurred only in the last few years. Recent environmental concerns and regulatory compliance coupled with water quality/quantity issues are resulting in a shift to using alternative water resources to care for turf. Paspalum will likely be the primary turfgrass to emerge in a new era of environmental stewardship, especially when using non-potable, alternative water resources. This is because seashore paspalum can exist under less than optimal conditions for extended periods of time. For example, seashore paspalum has excellent tolerance to saline (up to ocean salt water levels with some cultivars) or recycled water (such as alternative, gray, effluent, non potable, wastewater, and brackish water), good drought tolerance under proper management, can produce a high quality turfgrass with reduced nitrogen requirements, excellent wear tolerance, tolerates extended periods of low light intensity, such as prolonged cloudy or rainy periods, and tolerance to flooding or extended wet periods.

Unfortunately, seashore paspalum does not readily produce viable seed. Therefore, the only currently available method to establish seashore paspalum is vegetative propagation, for example by stolons, plugs, sod or sprigs. Such methods are expensive and time-consuming. Therefore, it is desirable to identify a seashore paspalum that is available from seed. Such a cultivar would reduce or eliminate the need to vegetatively establish seashore paspalum.

SUMMARY OF THE DISCLOSURE

Herein disclosed is a hybrid seashore paspalum that is available from seed. One example of such a seashore paspalum is termed 'Sea Spray'. As used herein, a seashore paspalum that is available from seed is a seashore paspalum grass plant that can be established by seed, thereby reducing or eliminating the need to vegetatively establish the seashore paspalum.

In one example, 'Sea Spray' seeds cover at least 20% of an area after 2 weeks when planted at 1 lb/1000 ft$^2$. In another example, 'Sea Spray' seeds cover at least 33-85% of an area after 4 weeks when planted at 1 lb/1000 ft$^2$.

Use of 'Sea Spray' grass as turf permits application of a wide range of water resources, including potable water and brackish as well as variable quality recycled water. The grass requires only minimal pesticides and judicious applications of fertilizers. It is efficient in the uptake and utilization of critical fertilizer nutrients.

'Sea Spray' has multiple uses in the turf industry. For example, it has the leaf texture, quality, and traffic tolerance for use on golf course greens, tees, fairways, and roughs; on sports fields including soccer, baseball, and football; in home lawn and business landscape areas; in municipal parks, and; on roadsides, such as in low drainage ways. 'Sea Spray' can be used to clean up polluted or contaminated waters or soils (phyto-remediation) and to transition into wetland sites or other environmentally sensitive areas to minimize the potential for point and non-point source pollution or contamination from industrial sites or other storm water collection problem areas.

At least 2500 seeds of hybrid 'Sea Spray' have been deposited with the American Type Culture Collection (ATCC, Manassas, Va., ATCC Deposit No. PTA-6827). Therefore, these seeds are known and readily available to the public.

In one example, the disclosure provides seashore paspalum plants that include the morphological and physiological characteristics of 'Sea Spray', as well as seeds of such plants. In some examples, the disclosure provides seashore paspalum plants having the genotype of 'Sea Spray'.

Methods of producing grass seed are also provided. The method includes growing 'Sea Spray' parents and producing progeny seed, and then harvesting the progeny seed. In some examples the method also includes planting seed from 'Sea Spray', under conditions that result in the germination of the seed and for the production of sod.

These and other aspects of the present disclosure will become more apparent from the following description.

DETAILED DESCRIPTION OF SEVERAL EMBODIMENTS

The following examples are provided to better describe the present disclosure and to guide those of ordinary skill in the art of the present disclosure. As used herein and in the appended claims, the singular forms "a" or "an" or "the" include plural references unless the context clearly dictates otherwise. For example, reference to "the seed" includes reference to one or more seeds and equivalents thereof known to those skilled in the art, and so forth. Similarly, the word "or" is intended to include "and" unless the context clearly indicates otherwise. Hence "comprising A or B" means including A, or B, or A and B.

Unless explained otherwise, all technical and scientific terms used herein have the same meaning as commonly understood to one of ordinary skill in the art to which this disclosure belongs.

EXAMPLE 1

Origin and Breeding History of Seashore Paspalum Hybrid 'Sea Spray'

The 'Sea Spray' seashore paspalum (*Paspalum vaginatum* O. Swartz) hybrid cultivar was developed by Pure Seed Testing, Inc. as part of a breeding program to develop a seashore paspalum cultivar that produces seed. The seashore paspalum ecotypes Q36313 and Hyb-7 were inter-planted as stolons in the same field in alternating rows for the first ¼ acre increase in Hubbard, Oreg. during the Fall 2001. The resulting hybrid seed produced from the (Q36313 and Hyb-7) cross is the $F_1$ generation of 'Sea Spray.' Production fields are now planted by alternating each parent plant within the row. Q36313 is a selection from Israel; Hyb-7 is a selection of unknown parentage. Certified seed is the result of $F_1$ seed resulting only from Q36313 crossed with Hyb-7. Production of 'Sea Spray' is limited to a single Certified generation of increase from Breeder sprigs or stolons. Pure Seed Testing, Inc. maintains breeder stolon beds for each parent in Oregon.

EXAMPLE 2

Seed Deposits

Seeds of the seashore paspalum hybrid 'Sea Spray' (Hyb. 7×Q36313) were deposited with the ATCC (Manassas, Va.) on Jul. 1, 2005 under accession number PTA-6827, under the terms of the Budapest Treaty. The cultivar is also maintained at, and available from, Pure Seed Testing, Inc., P.O, Box 449, Hubbard, Oreg. 97032.

EXAMPLE 3

Description of Plants

The following growth and morphological characteristics were observed for 'Sea Spray' plants that were approximately one year old, grown in the field near Hubbard, Oreg. Sprigs were planted in the fall 2001 of Q36313 and HYB-7. Seed of 'Sea Spray' was planted in the fall 2002. Morphological measurements were taken in 2002 for Q36313 and HYB-7 and in 2003 for 'Sea Spray'. Variations on the measurements shown in Table 1 may be observed for plants of differing ages, grown in other locations or under different weather conditions.

TABLE 1

Mean morphological measurements for 'Sea Spray' and parents.

| Feature | 'Sea Spray' | Q36313 | HYB-7 |
| --- | --- | --- | --- |
| Plant Height (cm) | 30.8 | 22.6 | 22.0 |
| Leaf Blade Length (mm) | 38.4 | 40.6 | 43.9 |
| Leaf Blade Width (mm) | 1.7 | 1.9 | 1.9 |
| Ligule Length (mm) | 1.0 | 0.9 | 1.0 |
| Leaf Sheath Length (mm) | 45.8 | 39.7 | 42.7 |
| Spikelet Length (mm) | 2.7 | 2.7 | 2.8 |
| Spikelets/1-cm Section (#) | 10.8 | 14.4 | 10.2 |
| Ligule Hair Length (mm) | 2.6 | 2.6 | 3.4 |
| Stolon Internode (mm) | 19.9 | 20.4 | 20.3 |
| Panicle Branches (#) | 2.3 | 2.4 | 2.5 |
| Longest Panicle Branch Length (mm) | 36.9 | 29.9 | 33.8 |
| Internode Length (mm) | 42.7 | 42.3 | 43.3 |
| Upper Internode Length (cm) | 56.8 | 36.9 | 51.0 |

EXAMPLE 4

Soil Coverage of Turf Grass Seeds

To compare the rate of establishment and grow-in to full canopy density coverage using the disclosed 'Sea Spray' seeds d to the amount of turf density coverage using seeds from other turf grasses, an establishment and grow in trial was performed at the University of Hawaii in Launiupoko, Maui, Hi., during April 2004.

Seeds were mixed with 15 handfuls of compost in a plastic bag, scattered by hand, watered for 10 minutes, and capped with hydromulch (200 lbs. paper mulch+3 lbs. C-Tack+50 lbs. compost+400 gal water) on Mar. 31, 2004. The fields were irrigated daily for 10 minutes at 4:30 am, 8 am, 10 am, 12 pm, 3 pm and 7 pm. However, irrigation coverage was not uniform due to strong trade winds. On Apr. 2, 2004, the field was fertilized with 10-30-10 at 4 lbs./1,000 ft$^2$; on Apr. 23, 2004 the field was fertilized with 21-7-14 at 1 lb/1,000 ft$^2$; and on May 30, 2004 the field was fertilized with 21-7-14 at 1 lb/1,000 ft$^2$.

The percent of turf density achieved after 2, 3, 4, and 5 weeks of planting was determined. As shown in Table 2, the rate of turf canopy coverage with 'Sea Spray' seeds was similar to most currently available turf grass seeds, and in many cases faster than other turf grass seeds.

TABLE 2

Percent soil coverage of various turf grass seeds.

| | | | % Soil Coverage (weeks after planting) | | | |
| --- | --- | --- | --- | --- | --- | --- |
| Variety | Label Rate per 1,000 ft$^2$ | Trial Rate per 1,000 ft$^2$ | April 14 2 weeks | April 21 3 weeks | April 28 4 weeks | May 4 5 weeks |
| Bermudagrass 'Cheyenne' | 0.5 lb | 1 lb | 40% | 60% | 93% | 88%* |
| Bermudagrass 'Mohawk' | 2-3 lbs. | 1 lb | 40% | 60% | 90% | 85%* |
| Bermudagrass 'Princess' | 1-2 lbs | 1 lb | 40% | 50% | 95% | 90%* |
| Buffalograss 'Cody' | 3 lbs. | 3 lbs | 30% | 40% | 40% | 80% |
| Buffalograss 'Cody' + | 3 lbs | 3 lbs | 25% | 30% | 40% | 75% |

TABLE 2-continued

Percent soil coverage of various turf grass seeds.

| Variety | Label Rate per 1,000 ft$^2$ | Trial Rate per 1,000 ft$^2$ | % Soil Coverage (weeks after planting) | | | |
|---|---|---|---|---|---|---|
| | | | April 14 2 weeks | April 21 3 weeks | April 28 4 weeks | May 4 5 weeks |
| 'Bison' Centipedegrass | 2-4 lbs | 1 lb | 30% | 40% | 70% | 85% |
| Australian Carpetgrass | 2-4 lbs | 1 lb | 25% | 30% | 40% | 80% |
| Fescuegrass 'Plantation' | 8-10 lbs | 4 lbs | 30% | 40% | 50% | 78%* |
| Kikuyugrass AZ1 | 2-3 lbs | 1 lb | 40% | 70% | 80% | 70%* |
| Seashore paspalum 'Sea Spray' | n/a | 1 lb | 20% | 50% | 85% | 95% |
| Weeping Lovegrass | 3-10 lbs | 1 lb | 40% | 50% | 60% | 75%* |
| Zoysiagrass 'Zenith' | 1-1.5 lbs | 1 lb | 10% | 20% | 25% | 40% |
| Annual Rye 'Gulf' | 4-6 lbs | 4 lbs | 50% | 50% | 60% | 70%* |
| Annual Rye 'Gulf' + Bermudagrass 'NuMex Sahara' | ? | 1 lb 1 lb | 70% | 90% | 95% | 85%* |

*Half of the plot was mowed to remove the top growth to determine the actual % soil coverage.

EXAMPLE 5

Comparison of 'Sea Spray' Seeds to other Seashore Paspalum Plugs

To compare the amount of turf canopy coverage using the 'Sea Spray' seeds disclosed herein to the amount of turf canopy coverage using seashore paspalum plugs (Salam, SeaIsle 1 and SeaIsle 2000 cultivars), an establishment and grow in coverage trial was performed in Launiupoki, Maui, Hi. Current methods of propagating seashore paspalum involve the use of plugs. Plugs (3"×3" plugs spaced 1 foot apart with 36 plugs per plot) were planted on Feb. 25, 2004 and 'Sea Spray' seeds were planted on Mar. 12, 2004 at 1.0-lb/1,000 ft$^2$. Each trial was replicated three times.

As shown in Table 3, 'Sea Spray' seeds established at a rate similar to that of seashore paspalum plugs. Therefore, the disclosed seeds provide a new method for propagation and establishment of seashore paspalum.

TABLE 3

Percent soil coverage of seashore paspalum plugs and seed.

| Cultivar | Days After Planting | |
|---|---|---|
| | 47 days | 62 days |
| Salam | 61.7% | 96.0% |
| SeaIsle-1 | 65.0% | 90.0% |
| SeaIsle-2000 | 50.0% | 91.6% |
| 'Sea Spray'* | 63.3% | 98.6% |

*= 'Sea Spray' is seeded and the others are vegetative.

EXAMPLE 6

'Sea Spray' Seeding Rate Trial

To determine the germination rate of 'Sea Spray,' a seeding rate trial was performed at sea level in Kahului, Maui, Hi. on sandy, calcareous soil, pH 8.0. Seeds were planted on Apr. 15, 2004 at: a) 0.5-lb/1,000 ft$^2$; b) 1.0-lb/1,000 ft$^2$; c) 1.5-lb/1,000 ft$^2$; d) 2.0-lb/1,000 ft$^2$; and e) 3.0-lb/1,000 ft$^2$. The field was watered daily at 7 am, 12 pm, 1, 2, 3 and 4 pm for 3 minutes. Each seeding rate was replicated three times.

As shown in Table 4, seeding rates of 1 and 1.5 lb/ft$^2$ 'Sea Spray' provide acceptable germination and turf establishment rates. Full density was achieved in 8 weeks at all seeding rates.

TABLE 4

Germination and percent soil coverage

| Rate lb/ft$^2$ | Seedling/ft$^2$ | % Soil Coverage | | | | | |
|---|---|---|---|---|---|---|---|
| | | (21 Days) | (28 Days) | (35 Days) | (43 Days) | (49 Days) | (56 Days) | (63 Days) |
| 0.5 | 49.7 | 16.7% | 46.7% | 66.7% | 71.7% | 86.6% | 100% |
| 1.0 | 80.3 | 33.3% | 65.0% | 76.7% | 85.0% | 94.3% | 100% |
| 1.5 | 144.7 | 41.7% | 68.3% | 80.0% | 87.6% | 95.0% | 100% |
| 2.0 | 142.3 | 53.0% | 76.7% | 88.0% | 94.7% | 99.3% | 100% |
| 3.0 | 235.3 | 65.0% | 81.7% | 94.3% | 99.0% | 100% | 100% |

EXAMPLE 7

Production of Seashore Paspalum Available from Seed

'Sea Spray' is produced by planting stolons of parents Q36313 and HYB-7 under conditions that permit crossing of the parents. For example, the parents can be planted in alternate rows or by alternating each plant in the row. It is believed the pollen is quite heavy, will not move great distances. Ideally, the plants are grown in close proximity to each other to achieve adequate seed setting. Insects and honey bees are attracted to the spikes and apparently assist in seed fertilization by collecting 'Sea Spray' pollen. The F1 hybrid 'Sea Spray' seeds deposited with ATCC are Certified seeds and can be planted to produce the $F_2$ generation (which is genetically different from 'Sea Spray').

'Sea Spray' can also be planted as seed in sod production fields and vegetative propagules, such as sprigs, plugs, and sod, sold as 'the cultivar' by licensed or approved growers.

EXAMPLE 8

Exemplary Uses of 'Sea Spray'

The seashore paspalum cultivar 'Sea Spray' can be used in the same way as other turf grass cultivars, such as other seashore paspalum cultivars for turf. However, the ability of 'Sea Spray' to be produced from seed affords the hybrid 'Sea Spray' particular advantages over other seashore paspalum cultivars. For example, with current commercially available cultivars of seashore paspalum grasses, propagation of the cultivar requires vegetative propagation, for example by stolons, plugs, sod or sprigs. This is a costly and labor-intensive process. In contrast, the propagation of hybrid 'Sea Spray' can be achieved by seed, thereby reducing costs and labor.

In addition, the tolerance of 'Sea Spray' to non-traditional water sources, such as potable water, seawater, or recycled water, affords 'Sea Spray' particular advantages over other warm season turfgrass cultivars. For example, most turf grasses are sensitive to alternative water sources, such as those that include higher concentrations of salt. However, some communities are now mandating the use of alternative water sources in turf irrigation. Because 'Sea Spray' can tolerate such alternative water sources, it is a good choice for use in turf situations.

Having illustrated and described the principles of the disclosure in multiple embodiments and examples, it should be apparent to those skilled in the art that the disclosure can be modified without departing from such principles. The invention therefore encompasses all modifications coming within the spirit and scope of the following claims.

What is claimed is:

1. A seashore paspalum grass plant having all of the morphological and physiological properties of a grass plant grown from the seed deposited under American Type Culture Collection (ATCC) No: PTA-6827.

2. A method of producing sod, comprising growing the grass plant of claim 1 to produce the sod.

3. The method of claim 2, further comprising planting the sod in a golf course or sports stadium.

4. The method of claim 2, further comprising planting the sod in a golf course tee, a golf course fairway or a golf course rough.

5. The method of claim 2, further comprising planting the sod in a lawn.

6. The method of claim 2, further comprising planting the sod in an athletic field.

7. The method of claim 2, further comprising planting the sod in a park.

8. A method of producing a progeny of the grass plant according to claim 1, comprising crossing the grass plant of claim 1 with another grass plant, thereby producing progeny.

9. A vegetative sprig or clone of the grass plant of claim 1.

10. A grass seed deposited as ATCC No: PTA-6827.

11. A method of producing a seashore paspalum grass seed, comprising:

planting the seed of claim 10 to produce a grass plant; and harvesting seed from the grass plant.

* * * * *